US006197752B1

(12) United States Patent
Schmidt et al.

(10) Patent No.: US 6,197,752 B1
(45) Date of Patent: Mar. 6, 2001

(54) GLYCOMIMETICS AS SELECTIN ANTAGONISTS AND PHARMACEUTICALS HAVING ANTIINFLAMMATORY ACTIVITY PREPARED THEREFROM

(75) Inventors: Wolfgang Schmidt, Frankfurt; Ulrich Sprengard, Gustavsburg; Gerhard Kretzschmar, Eschborn; Horst Kunz, Mainz, all of (DE)

(73) Assignee: Glycorex AB, Lund (SE)

( * ) Notice: Subject to any disclaimer, the term of this patent is extended or adjusted under 35 U.S.C. 154(b) by 0 days.

(21) Appl. No.: 08/708,475

(22) Filed: Sep. 5, 1996

(30) Foreign Application Priority Data

Sep. 6, 1995 (DE) ............................... 195 32 902

(51) Int. Cl.[7] .............................. A61K 31/70; C07H 1/00

(52) U.S. Cl. ...................... 514/23; 536/1.11; 536/18.7; 536/124

(58) Field of Search ................... 536/1.11, 18.7, 536/124; 514/23

(56) References Cited

U.S. PATENT DOCUMENTS

| | | | |
|---|---|---|---|
| 4,446,312 | 5/1984 | Noyori et al. | 536/1.11 |
| 4,454,123 | 6/1984 | Noyori et al. | 514/23 |
| 5,324,663 | 6/1994 | Lowe | 435/320.1 |
| 5,639,734 | 6/1997 | Esko et al. | 514/25 |

FOREIGN PATENT DOCUMENTS

| | | |
|---|---|---|
| 94/24145 | 10/1994 | (WO). |
| 95/04526 | 2/1995 | (WO). |
| 95/04751 | 2/1995 | (WO). |

OTHER PUBLICATIONS

Uchiyama et al. Design and Synthesis of C–Linked Fucosides as Inhibitors of E–Selectin, *Bioorganic & Medicinal Chemistry*, 4(7): 1149–1165 (1996).
Fluka Chemika–BioChemika Catalog, Fluka Chemie AG, 1993, pp. 12 and 988.
Gould et al. *Biochemistry* 1981, 20, 6776–6781.
Petasis et al., *J. Am. Chem. Soc.* 1995, 117(23), 6394–5.
Kashman et al. *Tetrahedron* 1969, 25(18), 4617–31.
Budinsky, A.C. et al, Wiener Klinische Wochenschrift, 107/15 pp. 443–450 (1995).
Saiki, Ikuo et al, Int. J. Cancer, 65, pp. 833–839 (1996).
Berg et al., "L–Selectin–Mediated Lymphocyte Rolling On MAdCAM–1", *Nature*, vol. 366:695–698, (Dec. 1993).
Baumhueter et al., "Binding of L–Selectin To The Vascular Sialomucin CD34", *Science*, vol. 262:436–438, (Oct. 1993).
Moore et al., "The P–Selectin Glycoprotein Ligand From Human Neutrophils Displays Sialylated, Fucosylated, O–Linked Poly-N–Acetyllactosamine", *The Journal of Biological Chemistry*, vol. 269(37):23318–23327, (Sep. 1994).
Mulligan et al., "Protective Effects Of Oligosaccharides In P–Selectin–Dependent Lung Injury", *Nature*, vol. 364:149–151, (Jul. 1993).
Buerke et al., "Sialyl Lewis—Containing Oligosaccharide Attenuates Myocardial Reperfusion Injury In Cats", *J. Clin. Invest.*, vol.93:1140–1148 (Mar. 1994).
Brandley et al., "Structure—Function Studies On Selectin Carbohydrate Ligands. Modifications To Fucose, Sialic Acid and Sulphate As a Sialic Acid Replacement", *Glycobiology*, vol. 3(6):633–639, (1939).

(List continued on next page.)

*Primary Examiner*—Kathleen K. Fonda
(74) *Attorney, Agent, or Firm*—Foley & Lardner (57) ABSTRACT

The invention relates to novel mimetics of the tetrasaccharides sialyl- Lewis-X (SLeX) and sialyl- Lewis-A (SLeA) having an improved action as inhibitors of cell adhesion, specifically a compound of the formula I $$R^1 \cdots O \cdots (CH_2)_3 - (D)_m - E - (CR^3R^4)_p - CR^5X^1X^2,$$
$$(CHR^2)_n$$
$$HO$$

in which
$R^1$ is —H, —$CH_3$ or —$CH_2OH$,
$R^2$ is —H or —OH,
$R^3$, $R^4$ and $R^5$ independently of one another are —H, $C_1$–$C_4$-alkyl or —OH,
$R^6$, $R^7$, $R^8$, $R^9$ and $R^{10}$ independently of one another are —H or $C_1$–$C_4$-alkyl
D is —O—C(O)—, —C(O)—or —$NR^6$—C(O)—,
E is —$CR^7R^8$—, —$NR^7$—, or a nitrogen heterocycle of the formula

[structures: pyrrolidine, piperazine with $(CH_2)_q$, and imidazole] or n is 1 or 2,
m is 0 or 1,
p is an integer from 0 to 10,
q is 1 or 2 and
$X^1$ and $X^2$ independently of one another are —H, —$COOR^9$, —$NR^9R^{10}$, —OH, —$OSO_3H$, —$CH_2COOR^9$ or —$CH_2OSO_3H$ or together are =O,
to a process for preparing these compounds and to their use as pharmacological active compounds and diagnostic agents.

60 Claims, No Drawings

OTHER PUBLICATIONS

Yoshida et al., "Synthesis Of Chemically Modified Sialic Acid–Containing Sialyl–Le$^x$ Ganglioside Analogues Recognized By The Selectin Family", *Glycoconjugate Journal*, vol. 10:3–15, (1993).

Nelson et al., "Higher–Affinity Oligosaccharide Ligands For E–Selectin", *J. Clin. Invest*.vol. 91:1157–1166 (Mar. 1993).

Musser et al., "Structure–Activity Studies Based On The Sialyl Lewis X Epitope", *Trends in Receptor Research*, pp. 33–40, (1993).

Allanson et al., "The Synthesis Of Novel Mimics Of the Sialyl Lewis X Determinant", *Tetrahedron: Asymmetry*, vol. 5(11):2061–2076, (1994).

Drew et al., "C–Glycoside Syntheses II: Henry Condensation Of 4,6,–O–Alkylidene Pyranoses With A 1,3–Proton Transfer Catalyst—A Route To Blocked Aminomethyl–C–Glycosides", *Tetrahedron: Asymmetrie*, vol. 47(32):6113–6126, (1991).

Lewis et al., "Highly Steroselective Approaches To α–and β–C–Glycopyranosides", *J. Am. Chem. Soc.*, vol. 104:4976–4978, (1982).

Levy et al., "Synthesis Of Novel Fused Ring C–Glycosides", *Tetrahedron: Asymmetry*, vol. 5(11):2265–2268, (1994).

Bajorath et al., "CD62/P–Selectin Binding Sites For Myeloid Cells and Sulfatides Are Overlapping", *Biochemistry*, vol. 33:1332–1339, (1994).

Uchiyama et al., "Design And Synthesis Of Sialyl Lewis X Mimetics", *J. Am. Chem. Soc.*, vol. 117:5395–5396, (1995).

Bruneel et al., "Chemical Modification Of Pullulan: 2. Chloroformate Acitvation", *Polymer*, vol. 34(12):2633–2637, (1993).

Walz et al., "Recognition By Elam–1 Of The Sialyl–Le Determinant On Myeloid And Tumor Cells", *Science*, vol. 250:1132–1135 (Nov. 1990).

Aruffo et al., "CD62/P–Selectin Recognition Of Myeloid And Tumor Cell Sulfatides", *Cell*, vol. 67:35–44, (Oct. 1991).

Harlan, "Blood", *The Journal of The American Society Of Hematology*, vol. 65(3):513–525, (Mar. 1985).

Springer, "Adhesion Receptors Of The Immune System", *Nature*, vol. 346:425–434, (Aug. 1990).

Atherton et al., "Quantitative Investigations Of The Adhesiveness Of Circulating Polymorphonuclear Leucocytes To Blood Vessel Walls", *J. Physiol.*, vol. 222:447–474, (1972).

Menger et al., "Scope And Perspectives Of Intravital Microscopy—Bridge Over From In Vitro to In Vivo", *Immunology Today*, vol. 14(11):519–522, (1993).

Foster et al., "Production of Tnfα By LPS–Stimulated Murine, Rat And Human Blood And Its Pharmacological Modulation", *Agents Actions 38*, pp. C77–C79, (1993).

Chemical Abstracts vol. 125, No. 19, No. 248275, (Nov. 1996), abstract of Uchiyama et al. Bioorg. Med. Chem. 1996, 4(7), 1149–65.

GLYCOMIMETICS AS SELECTIN ANTAGONISTS AND PHARMACEUTICALS HAVING ANTIINFLAMMATORY ACTIVITY PREPARED THEREFROM

FILING HISTORY

The present application claims priority under 35 U.S.C. of §119 of German Application DE 19532902.3, filed Sep. 6,1995.

BACKGROUND OF THE INVENTION

The invention relates to novel mimetics of the tetrasaccharides sialyl- Lewis-X (SLeX) and sialyl-Lewis-A (SLeA), with improved action as inhibitors of cell adhesion, to a process for the preparation of these compounds and to their use as pharmacologically active compounds and diagnostic agents.

The circulation of blood cells, for example leukocytes, neutrophils, granulocytes and monocytes is, on the molecular level, a highly complex multistage process of which only individual steps are known (Review: T. A. Springer, Cell 76, 301–314,1994).

Very recent research results have shown that the recirculation of the lymphocytes, which is crucial in immune monitoring, and the localization of neutrophils and monocytes at inflammatory foci respond to very similar molecular mechanisms. Thus, in acute and chronic inflammatory processes, the leukocytes adhere to endothelial cells and migrate into the inflammatory focus and into the secondary lymphatic organs.

The leukocyte adhesion process involves numerous specific signal molecules, for example interleukins, leucotrienes and tumor necrosis factor (TNF), receptors coupled to their G protein, and, in particular, tissue-specific cell adhesion molecules, which ensure precisely controlled recognition of the immune cells and endothelial cells. The most important adhesion molecules involved in this process are the receptors and include the selectins (E-, P- and L-selectins), integrins and the members of the immunoglobulin superfamily.

The adhesion of leukocytes to endothelial cells, which is mediated by selectin receptors in the initial phase of inflammatory processes, is a natural and necessary immune response to various inflammatory stimuli and to damage to the vascular tissue.

The excessive adhesion of leukocytes and their infiltration into the effected tissue affects the progression of many acute and chronic diseases. For example, rheumatism, reperfusion injuries such as myocardial ischemia/infarction (MI), acute pneumonia after operative surgery, traumatic shock and stroke, psoriasis, dermatitis, ARDS (adult respiratory distress syndrome) and the restenosis occurring after surgical intervention (for example angioplasty and by-pass operations). Preventing or reducing the adhesion process at a very early stage of the inflammation, therefore, is a highly attractive and generally applicable concept for the pharmacological control of inflammatory diseases.

It is presently generally recognized that the tetrasaccharides sialyl-Lewis-X (SLeX) and sialyl-Lewis-A (SLeA), which occur as substructures of glycosphingolipids and glycoproteins on cell membranes, are able to function as ligands for all three selectin receptors. The literature describes a range of glycoproteins, mucins and glycolipids suitable for use as endogenous ligands of the selectins. These include the mucosal vascular addressin MadCAM-1 (Berg et al., Nature 1993, 366, 695) and the sialomucin CD34 (Baumhuter et al., Science 1993, 262, 436) for L-selectin, an O-linked polylactosamine sialomucin PSGL-1 on human neutrophils P-selectin (Moore et al., J. Biol. Chem. 1994, 269,23318) and N-linked sialoglycoproteins of the type ESL-1 for E-selectin (Vestweber et al., Cell Biol. 1993,121, 449).

The natural ligand having the structure of SLeX has already been successfully used in animal experiments in P-selectin-dependent lung injuries (M. S. Mulligan et al., Nature 1993, 364, 149) and in myocardial reperfusion injuries (M. Buerke et al., J. Clin. Invest. 1994, 93,1140). In primary clinical trials in the case of acute pneumonia the compound is to be employed in a dose of 1–2 grams per day per patient (communication from Cytel Corp./ La Jolla (Calif.) in the 2nd Glycotechnology Meeting/CHI in La Jolla/USA on May 16–18, 1994).

However, the specificity of these and other potential ligands for selectins in vivo has not yet been elucidated. The tetrasaccharides SLeX and SLeA which occur on selectin ligands represent only a substructure of the substantially more complex endogenous ligand structures and, owing to their very similar affinity for selectins, they cannot be used alone to explain a specific receptor binding.

The search for the specificity of the tetrasaccharide's SLeX and SLeA for selection has led to their preparation as pharmaceuticals in a various administrative forms. Moreover, the complexity of the endogenous ligand, of which SleX and SLeA is a substructure, has resulted in the search for mimetics having modfied structures from the natural ligand.

Efforts to obtain more strongly binding antagonists by structural variation of the ligand are an area of intense interest. The aim of such work is to provide more active antagonists which would also potentially be suitable for use in vivo at a low dose.

While the fucose and neuraminic acid units have been reported as crucial for the structure-activity relationship, their modification did not bring any significantly improved inhibition values. (B. K. Brandley et al., Glycobiology 1993, 3, 633 and M. Yoshida et al., Glycoconjugate J. 1993, 10, 3). Only when the glucosamine unit was varied (replacement of GlcNAc by glucose and azido and amino groups in position 2 of GlcNAc) was it possible to achieve a significantly increased affinity for the E-selectin receptor. Supra. In the case of the P-selectin receptor, in contrast, no improved binding was obtained. Supra.

In general, all successes to date in improving the binding affinity of SLeX derivatives and SLeA derivatives have been limited to the E-selectin receptor, since only weak inhibition effects have been found with the P-selectin receptor at inhibitor concentrations of about 1 mM (R. M. Nelson et al., J. Clin. Invest. 1993, 91, 1157).

The prior art relative to the binding affinity of modified SLeX/A structures for selectins is reviewed in Pharmacochem. Libr. 1993, 20 (Trends in Drug Research), pages 33–40.

In addition to the low binding affinity of these compounds for the selectins, however, they all comprise at least one unstable glycosidic linkage, which drastically limits the oral availability of these active compounds. This instability also greatly restricts the synthesis of different derivatives, since the sensitive glycosidic linkage, which has a tendency to be cleaved, imposes great restrictions on the reaction conditions. A wide variety of approaches have been taken to the synthesis of mimetics in order to obtain an increase in the stability.

However, an increase in the stability has been achieved by linking the side chain to the C-4 carbon of fucose via a C—C bond (Floyd et al., Tetrahedron Asymmetry 1994, 5, 2061).

Figure 1:
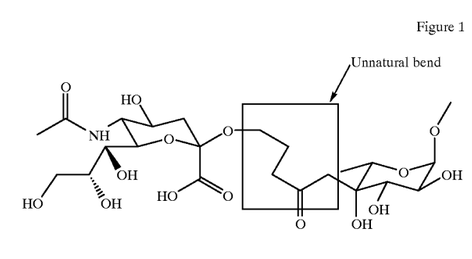

Unfortunately, the linkage to C-4 of fucose also causes the orientation of the side chain to deviate from that of the natural ligand, as indicated in FIG. 1. As a result, only a very small affinity was evident for binding to the selectins.

Figure 1

The use of carbacyclic carbohydrate analogs in which the linkage of the side chain is by a C—C bond to C-1 would result in a conformation similar to that of the natural ligand, but yet would be stable to degradation. Work is being carried out with great intensity on the preparation of carbacyclic carbohydrate analogs of monosaccharide units.

Among the various methods those worthy of emphasis are the reactions of activated monosaccharides with nitromethane (Gross P. H., Tetrahedron 1991, 47,6113), allylsilane (Y. Kishi et al., J. Am. Chem. Soc. 104, 4976–4978, 1982) and olefins (D. A. Levy et al., Tetrahedron Asymmetry 5, 2265–2268, 1994).

The use of a carbacyclic analog as a building block for selectin antagonists led to a mimetic with affinity for selecting. In this context it was possible by reacting a fucose unit with allylsilane to synthesize a specific C-glycosidic unit 1 with a orientation of the side chain (WO 95/04751). With a/β=14/1, the selectivities in the allylation are very good, but the proposed reaction conditions would not be readily amenable to scale up. Likewise, chromatographic purification, while necessary to purify the starting material, cannot be used to resolve the a/β mixture.

1

The terminal acid function of the side chain of compound 1 is the attachment site for glycopeptide analogs, for example compound 2. The derivatives have $IC_{50}$ values in the region of up to 1 mM. However, the glycopeptide analogs are unstable to the degradation of the peptide chain by proteases, so that the oral availability of these compounds is also highly limited. A further disadvantage is that the β compound cannot be separated off in this synthesis. This is problematic because the β derivatives are inactive as a result from the side chain having the wrong orientation, as demonstrated by corresponding model calculations.

2

In an analogous manner, the C-glycosidic unit 1 has also been used to synthesize various other mimetics which are intended to imitate the active conformation of $SLe^x$. The compounds tested, for example compound 3, however, had $IC_{50}$ values which at 10–20 mM were higher by a factor of 10–20 than that of the natural ligand $SLe^x$ (Wong et al., J. Am. Chem. Soc. 1995,117, 5395).

3

By using a substituted allylsilane it was possible to prepare the C-glycoside 4.

4

The triterpenoid acid derivative mimetics (betulinic acid: WO 95/04526; glycyrrhetinic acid: WO 94/24145) indicated by compound 4a were prepared and have multiple therapeutic effect. These compounds were tested and shown to display inhibition of 5-lipoxygenase, antimetastatic action and P-selectin inhibition. In these tests, the $IC_{50}$ found for binding to P-selectin was 0.75 mM. However, it should be noted here that the triterpenoid acid alone gives values of 0.125 mM in this test.

The preparation of the C-glycoside unit in 4 also requires a complex chromatographic purification in the course of which the β derivative can be separated only with difficulty. Moreover, the stability of the C-glycoside is reduced by the reactive allyl chloride group.

In addition to the preparative problems already described (complex chromatographic purification, high number of synthetic steps owing to the protective-group strategy, and the resolution of a/β mixture), the abovementioned C-glycoside mimetics have a binding affinity for the selectins which is too small for them to intervene effectively in the adhesion processes. The reason for this is two-fold. First, the stability of a fucose mimetic as a freestanding molecule means that it will be less reactive. Second, the orientation and conformative fixation of the side chain in the aforementioned derivatives is not optimized for selectin binding. The importance of the side chain conformation is emphasized by Wong et al., where slight changes in the structure of the side chain have marked effects on the binding strength (O—C exchange).

According to L. A. Lasky, negatively charged sialic acid (or a negatively charged sulfonic acid group) is important for binding to selectins. Since the crystal structure of E-selectin has been clarified, investigations concerning possible binding sites have already been carried out. For example, sialic acid can be bound at lysines K111 and K113 (J. Bajorath et al., Biochemistry 1994, 33, 1332) as well as at Arg 97, Lys111 and Lys113 (Structural Biology 1, 140 (1994)).

SUMMARY OF THE INVENTION

It is the object of the present invention to provide stable, low molecular mass glycomimetics of the sialyl-Lewis-X and, sialyl-Lewis-A structures, respectively, and pharmacuetical compositions comprising said glycomimetics which possess a significantly increased affinity for selectins. The invention also provides an improved synthesis for glycomimetics over those currently known for oligosaccharides. Finally, the invention provides the use of said glycomimetics and compositions comprising them as pharmaceuticals.

These objects are achieved by a compound and its physiologically-compatible salts of the formula I:

wherein:

$R^1$ is —H, —$CH_3$ or —$CH_2OH$, $R^2$ is —H or —OH, $R^3$, $R^4$ and $R^5$ independently of one another are —H, $C_1$-$C_4$-alkyl or —OH, $R^6$, $R^7$, $R^8$, $R^9$ and $R^{10}$ independently of one another are —H or $C_1$-$C_4$-alkyl, D is —O—C(O)—, —C(O)— or —$NR^6$—C(O)—, E is —$CR^7R^8$—, —$NR^7$—, or a nitrogen heterocycle of the formula:

n is 1 or 2, m is 0 or 1, p is an integer from 0 to 10, q is 1 or 2 and $X^1$ and $X^2$ independently of one another are —H, —$COOR^9$, —$NR^9R^{10}$, —OH, —$OSO_3H$, —$CH_2COOR^9$ or —$CH_2OSO_3H$ or together are =O.

Preferably, in formula I m is 1 and D is —O—C(O)—, and m is 0.

In a further preferred embodiment, the invention relates to compounds and their physiologically compatible salts of the formula:

wherein D, E, $R^3$, $R^4$, $R^5$, $X^1$, $X^2$, m & p are as defined previously.

Amongst the most preferred compounds of this embodiment are compounds of the formula:

A—$(CH_2)_3$—$(D)_m$—E—$(CR^3R^4)_p$—$CR^5X^1X^2$;

wherein D, E, $R^3$, $R^4$, $R^5$, $X^1$, $X^2$, m & p are as defined previously and A is a sugar radical selected from the group consisting of:

or

The invention also relates to a process for preparing a compound of formula I, which comprises the following steps performed on a compound of formula III:

III wherein:

R$^1$, R$^2$ and n are as defined above, R$^1$ and R$^2$ being provided if necessary with protecting groups, and R is an acetyl group, a) reacting with an allylsilane in the presence of a Lewis acid catalyst in an appropriate solvent to form a compound of formula IV:

IV wherein

R, R$^1$ and R$^2$ and n are as defined above;

b) converting the R acetyl protecting group to a benzyl group, followed by;

c) functionalizing the allylic double bond to prepare a compound of formula V:

V wherein R$^1$ and R$^2$ are as defined above and are provided if necessary with protecting groups, R is a benzyl group and Y is halogen or an OH group;

d) reacting the compound of formula V with a compound of the formula:

X—E—(CR$^3$R$^4$)$_p$—CR$^5$X$^1$X$^2$ wherein X is —H or —COOH, E, R$^3$, R$^4$, R$^5$, X$^1$, X$^2$ and p are as defined above; and e) removing the protecting groups, if present.

The activated OH group Y can advantageously be produced by reacting the free OH group with p-nitrophenyl chloroformate (Polymer 34, 26–33 (1993)).

The compounds of the present invention and their physiologically compatible salts are highly suitable, owing to their valuable pharmacological properties, for use as medicaments for mammals, especially humans.

The present invention additionally provides a pharmaceutical composition comprising the compound of the formula I with a pharmaceutically-acceptable excipient, and for their use as treatments for the prophylaxis of diseases which accompany excessive, selectin receptor-mediated cell adhesion in the tissue affected by the disease. For example rheumatism, reperfusion injuries, ischemia or myocardial infarction.

The compounds and pharmaceutical compositions of the present invention are particularly suitable for treating acute and chronic inflammation which is marked pathophysiologically by a disruption in the circulation of cells, for example of lymphocytes, monocytes and neutrophil granulocytes. Included in this context are autoimmune diseases such as acute polyarthritis, rheumatoid arthritis and insulin-dependent diabetes mellitus (IDDM), acute and chronic transplant rejections, ARDS (adult respiratory distress syndrome), inflammatory and allergic skin diseases, for example psoriasis and contact eczema, cardiovascular diseases such as myocardial infarction, reperfusion injuries after thrombolysis, angioplasty or bypass operations, septic shock and systemic shock Additionally, the compounds and compositions would be expected to have particular effectiveness against surface antigens which possess both sialyl-Lewis-X and sialyl-Lewis-A structures as recognition epitopes.

For example, metastatic tumors, as described by A. C. Budinsky et al., *Wiener klinische Wochenschrift* 107:15, 443–450 (1995) and I. Saiki et al, *Int J. Cancer* 65, 833–838 (1996).

DETAILED DESCRIPTION OF THE INVENTION

As used herein, the term "C$_{1-4}$ alkyl" means a straight or branched chain alkyl group from one to four carbon atoms. For example, methyl, ethyl, n-propyl, isopropyl, n-butyl, s-butyl, t-butyl.

As used herein, the term "physiologically-compatible salt" means is well known to one of ordinary skill in the art and is intended to mean any organic or inorganic acid salt which is capable of forming a non-toxic addition salt which is suitable for use as a pharmaceutical. Illustrative inorganic acids which form suitable salts include hydrochloric, hydrobromic, sulphuric, and phosphoric acid and acid metal salts such as sodium monohydrogen orthophosphate, and potsssium hydrogen sulfate. Illustrative organic acids which form suitable salts, include the mono-, di- and tri-carboxylic acids. For example, acetic, glycolic, lactic, pyruvic, malonic, succinic, glutaric, fumaric, malic, tartaric, citric, ascorbic, maleic, hydroxymaleic, hydroxybenzoic, phenylacetic, cinnamic, salicylic, glutamic, gluconic, formic and sulfonic acids such as methane sulfonic acid and 2-hydroxyethane sulfonic acid. Further examples of suitable physiologically-compatible salts are recited in Berge S. M. et al., J. Pharm. Sci. 66:1,1 (1977), which is herein incorporated by reference. Such salts can exist in either a hydrated or substantially anhydrous form.

As used herein, the term "Lewis and catalyst in an appropriate solvent" means an compound that can combine with another molecule by forming a covalent bond with two electrons from the second compound. For example, boron trifluoride etherate in acetonitrile or trimethylsilyl trifluoromethanesulfonate (trimethylsilyl triflate) in nitromethane.

The pharmaceuticals according to the invention are generally administered intravenously, orally, parenterally or as implants, although rectal administration is also possible in principle. Examples of suitable solid or liquid pharmaceutical preparation forms are granules, powders, tablets, film-coated tablets, microcapsules, suppositories, syrups, emulsions, suspensions, aerosols, drops or injectable solutions in ampule form, and also preparations with protracted release of active compound, the preparation of which commonly employs excipients and additives and/or auxiliaries such as disintegrants, binders, coating agents, swelling agents, glidants or lubricants, flavorings, sweeteners or solubilizers. By "pharmaceutically-acceptable excipient" it is intended, for example, magnesium carbonate, titanium dioxide, lactose, mannitol and other sugars, talc, lactoprotein, gelatin, starch, vitamins, cellulose and derivatives thereof, animal and vegetable oils, polyethylene glycols and solvents, for instance sterile water, alcohols, glycerol and polyhydric alcohols. The term "pharmaceutically-acceptable excipient" expressly includes one or more of the above described excipients.

The pharmaceutical preparations are preferably prepared and administered in dosage units. Solid dosage units are tablets, capsules and suppositories.

For the treatment of a patient, different daily doses are required depending on the effectiveness of the compounds, on the mode of administration, on the nature and severity of the disease and on the age and body weight of the patient. Under certain circumstances, however, higher or lower daily doses may also be appropriate, as is readily determinable to one or ordinary skill in the art. The daily dose can be administered either as a single dosage unit or as a plurality of small dosage units, or else by the repeat administration of part-doses at defined intervals. The daily dose to be administered may additionally in part be dependent on the number of receptors expressed during the course of the disease. This would be expected because in the initial stage of the disease only a few receptors are expressed on the cell surface, and consequently the daily dose to be administered is lower than in the case of severely affected patients.

The following text provides generally how the compounds of the present invention may be made.

I. CHEMICAL SYNTHESIS

The following scheme provides for the synthesis of the pure a-C-glycoside 8 in only 3 stages with an overall yield of 72% (scheme).

L-fucose 5 is acetylated with acetic anhydride/pyridine (95–98%) and subsequently reacted with an allylsilane employing catalysis by $BF_3$ (92%, a/β ratio 10:1). The resulting C-glycoside 7 was deacylated (quantitatively) and purified by recrystallization. By appropriate choice of recrystallization conditions it was possible to obtain the a-derivative 8 in pure form.

The C-glycoside 8 can be employed for functionalizing and fixing the side chain. This may be accomplished by protection of the hydroxyl groups in compound 8 by benzylation followed by hydroboration with borane to give the alcohol 10 in 63% yield. The alcohol 10 is converted with triphenylphosphine/dibromotetrachloroethane, with a yield of 92%, into the bromide 11.

The alcohol 10 and the bromide 11 are suitable building blocks for the synthesis of the side chain which is required for binding (see Example compounds 12 a–d and 13a,b). The alcohol 10 is activated, for example by conversion into an active ester.

The reactions can be transferred analogously to other C-glycoside units, for example compound 14, which can be prepared from D-mannose, or compound 20, which can be prepared starting from ribose by way of compound 19. In a similar manner the above process can be used to prepare derivatives of L-galactose, L-rhamnose and glucose.

Particular compounds of the invention can be produced analogously to the process described above, and are defined when the variables of formula I are:

1. E is —NR$^7$—, R$^7$ is —H, p is 0, R$^5$ is —H, X$^1$ is —COOR$^9$, X$^2$ is —CH$_2$COOR$^9$ and R$^9$ is —H, for example:

2. E is —NR$^7$—, R$^7$ is —H, p is 4, R$^3$ and R$^4$ are —H R$^5$ is —H, X$^1$ is —COOR$^9$, X$^2$ is —NR$^9$R$^{10}$ and R$^9$ and R$^{10}$ are —H, for example:

3. E is a heterocycle of the formula:

q is 2, p is 0, $R^5$ is —OH and $X^1$ and $X^2$ together are =O, for example:

4. E is a heterocycle of the formula:

q is 2, p I s 0, $R^5$ and $R^9$ are —H and $X^1$ and $X^2$ are —$COOR^9$, for example:

or

II. BIOLOGICAL ASSAYS

Primary assays for investigating the action of the compounds according to the present invention on cell adhesion to recombinant, soluble selectin fusion proteins.

In order to test the activity of the novel compounds on the interaction between the E- and P-selectins (former nomenclature ELAM-1 and GMP-140 respectively,) with their ligands, an assay is used which is specific in each case for only one of these interactions. The ligands are supplied in their natural form as surface structures on promyelocytic HL60 cells. Since HL60 cells contain ligands and adhesion molecules of very different specificity, the desired specificity of the assay can only be brought about by means of the binding component. The binding components used were genetically prepared soluble fusion proteins from, in each case, the extracytoplasmatic domains of E- or P-selectin and the constant region of a human immunoglobulin of the IgG1 subclass.

Preraration of L-selectin-IgG1

For the preparation of soluble L-selectin-IgG1 fusion protein, the genetic construct "ELAM-Rg" published by Walz et al., 1990, was used.

For expression, the plasmid DNA was transfected in COS-7 cells (ATCC) by means of DEAE-dextran (molecular biology methods: see Ausubel, F. M., Brent, R., Kingston, R. E., Moore, D. D., Seidman, J. G., Struhl, K. and Smith, J. A. 1990. Current Protocols in Molecular Biology, John Wiley, New York). Seven days after transfection, the culture supernatant is recovered, freed from cells and cell fragments by centrifugation and transferred to 25 mM HEPES pH 7.0, 0.3 mM PMSF, 0.02% sodium azide and stored at +4° C. (Walz, G., Aruffo, A., Kolanus, W., Bevilacqua, M. and Seed, B. 1990. Recognition by ELAM-1 of the sialyl-Lex determinant on myeloid and tumor cells. Science 250, 1132–1135.)

Preparation of P-selectin-IgG1

To prepare the soluble P-selectin-IgG1 fusion protein, the genetic construct "CD62Rg" published by Aruffo et al., 1991, is used. The subsequent procedure corresponds to the preparation of L-selectin-IgG1 presented in Table 1.

Aruffo, A., Kolanus, W., Walz, G., Fredman, P. and Seed, B. 1991. CD62/-P-Selectin recognition of myeloid and tumor cell sulfatides. Cell 67, 35–44.

Preparation of CD4-IgG1

For the preparation of the soluble CD4-IgG1 fusion protein, the genetic construct "CD4:IgG1 hinge", published by Zettlemeissl et al., 1990, is used. The subsequent procedure corresponds to the preparation of L-selectin-IgG1 presented under A1. (Zettelmeissl, G., Gregersen, J. P., Duport, J. M., Mehdi, S., Reiner, G. and Seed, B. 1990. Expression and characterization of human CD4: Immunoglobulin Fusion Proteins. DNA and Cell Biology 9, 347–353.) The procedure is carried out the HL60 cell adhesion assay on recombinant, soluble adhesion molecules:

1. 96-well microtiter assay plates (Nunc Maxisorb) are incubated at room temperature for 2 hours with 100 ml of a goat anti-human IgG antibody (Sigma) diluted (1+100) in 50 mM Tris pH 9.5. After removing the antibody solution, washing is carried out once with PBS.
2. 150 ml of the blocking buffer are left in the wells at room temperature for 1 hour. The composition of the blocking buffer is as follows: 0.1% gelatin, 1% BSA, 5% calf serum, 0.2 mM PMSF, 0.02% sodium azide. After removing the blocking buffer, washing is carried out once with PBS.
3. 100 ml each of cell culture supernatant from appropriately transfected and expressing COS cells are pipetted into the wells. Incubation is carried out at room temperature for 2 hours. After removing the cell culture supernatant, washing is carried out with PBS.
4. 20 ml of binding buffer are added to the wells. The binding buffer has the following composition: 50 mM HEPES, pH 7.5; 100 mM NaCl; 1 mg/ml BSA; 2 mM $MgCl_2$; 1 mM $CaCl_2$; 3 mM $MnCl_2$; 0.02% sodium azide; 0.2 mM PMSF. 5 ml of the test substance are added by pipette, mixed by swirling the plate and incubated at room temperature for 10 minutes.
5. 50 ml of an HL60 cell culture containing 200,000 cells/ml are centrifuged at 350 g for 4 minutes. The pellet is resuspended in 10 ml of RPMI 1640 and the cells are centrifuged again. In order to label the cells, 50 mg of BCECF-AM (Molecular Probes) are dissolved in 5 ml of anhydrous DMSO; then 1.5 ml of RPMI 1640 are added to the BCECF-AM/DMSO solution. The cells are resuspended using this solution and incubated at 37° C. for 30 minutes. After centrifugation at 350 g for two minutes the labeled cell pellet is resuspended in 11 ml of binding buffer and the resuspended cells are distributed into the microtiter plate wells in 100 ml aliquots. The plate is allowed to stand at room temperature for 10 minutes in order to allow the cells to sediment on the bottom of the test plate. In the course of this operation the cells have the opportunity to adhere to the coated plastic.

6. To stop the assay, the microtiter plate is immersed completely in the stop buffer (25 mM Tris, pH 7.5; 125 mM NaCl; 0.1% BSA; 2 mM $MgCl_2$; 1 mM $CaCl_2$; 3 mM $MnCl_2$; 0.02% sodium azide) at an angle of 45°. The stop buffer is removed from the wells by inversion and the procedure is repeated twice more.
7. Measurement of the BCECF-AM-labeled cells adhering firmly in the wells is carried out in a cytofluorimeter (Millipore) at a sensitivity setting of 4, an excitation wavelength of 485/22 nm and an emission wavelength of 530/25 nm.

TABLE 1

| | E-and P-selectin binding | |
|---|---|---|
| Compound | $IC_{50}$ E-Selectin (mM) | $IC_{50}$ P-Selectin (mM) |
| 12a | 5 | 10 |
| 12b | 5 | 10 |
| 12c | 3 | 10 |
| 12d | 5 | 10 |
| 13a | 10 | 10 |

Leukocyte Adhesion—Testing the Activity of the Novel Compound in vivo

In inflammatory processes and other states which activate the cytokines, a critical part is played by the destruction of tissue by means of leukocytes which migrate in or which block the microcirculation. The first phase, which is critical for the subsequent course of the disease, is the activation of leukocytes within the blood stream, especially in the pre- and post-capillary area. This results, after the leukocytes have left the axial flow of the blood, in initial adhesion of the leukocytes to the inner vessel wall, i.e. on the vascular endothelium. All subsequent leukocyte effects, i.e. active migration through the vessel wall and subsequent oriented migration in the tissue, are secondary reactions (Harlan, J. M., Leukocyte-endothelial interaction, Blood 65, 513–525, 1985).

This receptor-mediated interaction of leukocytes and endothelial cells is regarded as an initial sign of the inflammation process. In addition to the merely physiologically expressed adhesion molecules, under the action of inflammation mediators (leukotrienes, PAF) and cytokines (TNF-alpha, interleukins) there is massive, chronologically graduated expression of adhesion molecules on the cells. They are currently subdivided into three groups: 1. immunoglobulin gene superfamily, 2. integrins and 3. selectins. Whereas adhesion between molecules of the Ig gene superfamily takes place by way of protein-protein bonds, in the case of cooperation between selectins it is lectin-carbohydrate bonds which are principally involved (Springer, T. A., Adhesion receptors of the immune system. Nature 346, 425–434, 1990; Huges, G., Cell adhesion molecules—the key to a universal panacea, Scrips Magazine 6, 30–33,1993; Springer, T. A., Traffic signals for lymphocyte recirculation and leukocyte emigration; The multistep paradigm. Cell 76, 301–314,1994).

Method:

The induced adhesion of leukocytes is quantified by an investigation technique involving intravital microscopy in the mesenterium of the rat (Atherton A. and Born G.V.R., Quantitative investigations of the adhesiveness of circulating polymorphonuclear leukocytes to blood vessel walls. J. Physiol. 222, 447–474,1972; Seiffge, D. Methoden zur Untersuchung der Rezeptor-vermittelten Interaktion zwischen Leukozyten und Endotheizellen im Entzündungsgeschehen [Methods of investigating receptor-mediated interaction between leukocytes and endothelial cells in the case of inflammation] in: Ersatz- und Ergänzungsmethoden zu Tierversuchen in der biomedizinischen Forschung, Schöffl, H. et al., (eds.) Springer, 1995 (in press)). Under ether-inhalation anesthesia, long-term anesthesia is induced by intramuscular injection of urethane (1.25 mg/kg BW). After exposure of vessels (the femoral vein for the injection of substances and the carotid artery for measurement of blood pressure), catheters are inserted into these vessels and fastened. Then the corresponding transparent tissue (mesenterium) is exposed by the standard methods known from the literature, transferred to the microscope stage and covered with a layer of hot paraffin oil at 37° C. (Menger, M. D. and Lehr, H., A. Scope and perspectives of intravital microscopy-bridge over from in vitro to in vivo, Immunology Today 14, 519–522,1993). The test substance is administered intravenously (10 mg/kg). The experimental increase in blood cell adhesion by systemic administration of lipopolysaccharide (LPS, 15 mg/kg) is initiated 15 minutes after administration of test substance by cytokine activation (Foster S. J., McCormick L. M., Ntolosi B. A. and Campbell D., Production of TNF-alpha by LPS-stimulated murine, rat and human blood and its pharmacological modulation, Agents and Actions 38 C77–C79, 1993, 18.01.1995). The resulting increased adhesion of leukocytes on the endothelium is quantified directly by vital microscopy or with the aid of fluorescent dyes. All measurement operations are recorded by video camera and stored on a video recorder. Over a period of 60 minutes, the number of rolling leukocytes (i.e. all visibly rolling leukocytes, which are slower than the flowing erythrocytes) and the number of leukocytes adhering to the endothelium (for more than 5 seconds) are detected every 10 minutes. After the end of the experiment, the anesthetized animals are euthenized by systemic injection of T61. For evaluation, the results of 4 treated animals are compared in each case with those of 4 untreated animals in Table 2 and expressed as a percentage of inhibition of leukocyte adhesion.

TABLE 2

| | | | | | | | | | |
|---|---|---|---|---|---|---|---|---|---|
| | | | | | | | | Leukocyte Adhesion | |
| comp. | dose (mg/kg) | dose type | species | mean weight (g) | number of vessels | vessel diam. | leukocytes $10^3/mm^3$ | fibrinogen (mg/100 mL) | inhibition of adhesion |
| 12c | 3 | 1 day i.v. | SPRD (m) | 229 +/− 28.6 | 15 | 24 +/− 2.7 | 8.7 +/− 0.9 | 109 +/− 16.6 | 58% |
| 12c | 20 | 1 day p.o. | SPRD (m) | 255 +/− 23.2 | 15 | 24 +/− 4.2 | 7.6 +/− 2.2 | 137 +/− 10.0 | 29% |

TABLE 2-continued

Leukocyte Adhesion

| comp. | dose (mg/kg) | dose type | species | mean weight (g) | number of vessels | vessel diam. | leukocytes $10^3/mm^3$ | fibrinogen (mg/100 mL) | inhibition of adhesion |
|---|---|---|---|---|---|---|---|---|---|
| 12c | 50 | 17 days p.o. | Lewis (m) | 237 +/− 22.7 | 18 | 28 +/− 3.9 | 16.7 +/− 3.2 | 249 +/− 64.8 | 74% |
| 12c | 50 | 17 days p.o. | Lewis (m) | 218 +/− 10.8 | 18 | 26 ± /−3.8 | 19.1 +/− 2.5 | 242 +/− 55.3 | 11% |

The following examples are intended to further illustrate the preparation of particular example compounds of the invention, and should not be construed as limiting the invention in any way.

EXAMPLES

Example 1

Preparation of the C-glycoside Units 10 and 11
Acetylation of Fucose

Pyridine (616 ml, 7.62 mol) and acetic anhydride (633 ml, 6.7 mol) are added to L-fucose 5 (250 g, 1.52 mol) and the mixture is stirred at room temperature for 24 hours. The solvent is removed on a rotary evaporator and the residue is dried under high vacuum. Compound 6 (496 g, 98%) is obtained as a yellow oil.

TLC [hexane/ethyl acetate:1/1]: $R_f$=0.60.-$^1$H-NMR (300 MHz, CDCl$_3$): d=1.18 (d, 3H, $J_{6.5}$=6.9 Hz, 6-H$^{Fuc}$), 2.00–2.15 (4 s,12H, CH$_3$), The fucose derivative 6 (50 g, 0.15 mol) is dissolved in acetonitrile (300 ml) under argon and cooled to −10° C. Following the addition of allylsilane (47.9 ml, 0.30 mol) and boron trifluoride-diethyl ether complex (20.4 ml, 0.166 mol) the mixture is stirred at −10° C. for 1 hour. After warming to room temperature it is stirred for a further 3 hours. The solution is poured into saturated hydrogen carbonate solution and subjected to extraction with ethyl acetate. The solvent is removed on a rotary evaporator. The residue which remains is taken up in dichloromethane and filtered through a short silica gel column. Removal of the solvent gives compound 7 (a/β10/1) as a yellow oil (43.5 g, 92%).

TLC [hexane/ethyl acetate:1/1]: $R_f$=0.65-$^1$H-NMR (300 MHz, CDCl$_3$): d=1.19 (d, 3H, $J_{6.5}$=6.9 Hz, 6-H$^{Fuc}$), 2.00–2.15 (3 s, 9H, CH$_3$), 2.20–2.58 (m,2H), 3.98 (m,1M ), 4.28 (m, 1H), 5.05–5.85 (m, 6H).

The allyl derivative 7 (43.5 g, 0.139 Mol) is dissolved in methanol (200 ml), and sodium methanolate solution (3 ml, 30% strength) is added. The solution is stirred at room temperature for 2 hours and neutralized with acidic ion exchanger (Dowex 50 W X 8). The ion exchanger is removed by filtration and the solvent is stripped off on a rotary evaporator. The deacetylated fucose derivative is obtained as a pale yellow solid (26.0 g, quantitative).

The residue is dissolved with heating in ethyl acetate and filtered while hot. Following removal of the solvent on a rotary evaporator the residue is dissolved again with heating in wet ethyl acetate. When the solution is cooled, compound 8 crystallizes out as a white solid (20.8 g, 80%).

TLC [dichloromethane/methanol:10/1]: $R_f$=0.25-$^1$H-NMR (300 MHz, D$_3$O): d=1.05 (d, 3H, $J_{6.5}$=6.9 Hz, 6-H$^{Fuc}$), 2.19–2.43 (m, 2H), 3.60–4.00 (m, 5H), 5.05 (m, 2H), 5.62–5.80 (m, 1H).

A solution of compound 8 (5.0 g, 27.0 mmol) in DMF (5 ml) is added slowly dropwise at 0° C. under argon to a suspension of sodium hydride (95%, 2.27 g, 95 mmol) in DMF (40 ml). The mixture is stirred at this temperature for 30 minutes. Benzyl bromide (10.3 ml, 86.5 mmol) is added dropwise. After 1 hour the mixture is warmed to room temperature and stirred at room temperature for 12 hours more. Following the careful addition of methanol and water, extraction is carried out with ethyl acetate. The organic phase is washed a number of times with water and dried over magnesium sulfate. Removal of the solvent on a rotary evaporator gives an oily residue which is purified by flash chromatography (isohexane/ethyl acetate 4/1–1/1). 9 (9.1 g, 19.9 mmol, 74%) is obtained as a colorless oil:

TLC [toluene/ethyl acetate:1/1]: $R_f$=0.55-$^1$H-NMR (300 MHz, CDCl$_3$): d=1.15 (d, 3H, $J_{6.5}$=6.9 Hz, 6-H$^{Fuc}$), 2.22–2.45 (m, 2H), 3.78 (m, 3H), 3.90–4.40–410 (m, 2H), 4.40–4.80 (m, 6H), 5.00–5.12 (m, 2H), 5.80 (m, 1H), 7.30–7.40 (m, 15H).

The allyl compound 9 (9.1 g, 19.9 mmol) is dissolved in THF (40 ml) under argon, and the solution is cooled to 0° C., and a 1 M borane-THF (25 ml) solution is added dropwise at this temperature. After the end of the addition the solution is warmed to room temperature and stirred for 3 hours. The mixture is again cooled to 0° C., and 5 M NaOH solution (25 ml) and 30% strength hydrogen peroxide solution (20 ml) are added carefully. After extraction with ethyl acetate the solvent is removed on a rotary evaporator. The residue is purified by flash chromatography (isohexane/ethyl acetate 2/1–1/1). Compound 10 (8.05 g, 16.9 mmol, 85%) is obtained as a colorless oil.

The alcohol 10 (740 mg, 1.6 mmol) is dissolved in dichloromethane (10 ml) and the solution is cooled to 0° C. Triethylamine (230 ml, 6.4 mmol), triphenylphosphine (polymer-bound, 1.1 g, 3.2 mmol) and dibromotetrachloro-ethane (1.04 g, 3.2 mmol) are added in succession. The mixture is stirred at 0° C. until conversion is complete (1 hour), taken up in dichloromethane and washed with water. After removal of the solvent on a rotary evaporator the residue is purified by flash chromatography (isohexane/ethyl acetate 4/1–2/1). Compound 11 is obtained as a colorless oil (0.79 g, 1.47 mmol, 92%).

TLC [toluene/ethyl acetate:1/1]: $R_f$=0.85-$^1$H-NMR (300 MHz, CDCl$_3$): d=1.15 (d, 3H, $J_{6.5}$=6.9 Hz, 6-H$^{Fuc}$), 1.56–2.00 (m, 3H), 3.40 (m, 2H), 3.78 (m, 3 H, 3.80–4.00 (m, 3H), 4.40–4.80 (m, 6H), 7.30–7.40 (m, 15H).

Example 2

Procedure for Preparing the Carbamates 12a–d

The alcohol 10 is dissolved in dichloromethane (10 ml/mmol), and triethylamine (1.1 equivalents) is added.

p-Nitrophenyl chloroformate (1.3 equivalents) and a catalytic amount of DMAP are added at 0° C. The solution is stirred overnight and DIPEA (3 equivalents) and the amine component (1.5 equivalents) are added. The solution is stirred at room temperature for 10 hours more, taken up in dichloromethane and washed with saturated sodium hydrogen carbonate solution. Following removal of the solvent on a rotary evaporator the residue is dissolved in MeOH/dioxane/AcOH (5/1/1) and hydrogenated using Pd/C (10%) as catalyst (10 hours). After removal of the catalyst by filtration and removal of the solvent the oily residue is taken up in 1M sodium hydroxide solution (3–5 ml) and the mixture is stirred until hydrolysis is complete (2 hours). The mixture is purified by chromatography (Bakerbond, silica gel RP 18, 40 mm, methanol/water 10/90–90/10).

12a TLC [ethyl acetate/methanol/formic acid/water 5/3/0.5/1]: $R_f$=0.30-$^1$H-NMR (300 MHz, $D_2O$): d=1.05 (d, 3H, $J_{6,5}$=6.9 Hz, 6-$H^{Fuc}$), 1.60–1.95 (m, 2H), 1,96 (m, 1H), 3.78–10 (m, 8H), 4.58 (m, 1H).

12b TLC [ethyl acetate/methanol/formic acid/water 5/3/0.5/1]: $R_f$=0.35-$^1$H-NMR (300 MHz, $D_2O$): d=1.05 (d, 3H, $J_{6,5}$=6.9 Hz, 6-$H^{Fuc}$), 1.10–1.80 (m, 10 H), 300 (m, 2H), 3.57–4.05 (8H).

12c TLC [ethyl acetate/methanol/formic acid/water 5/3/0.5/1]: $R_f$=0.25-$^1$H-NMR (300 MHz, $D_2O$): d=1.5 (d, 3H, $J_{6,5}$=6.9 Hz, 6-$H^{Fuc}$), 1.25–1.80 (m, 7H), 2.4(m, 1H), 2.80 (m, 2H), 3.60–4.05 (m, 9H).

12d TLC [ethyl acetate/methanol/formic acid/water 5/3/0.5/1]: $R_f$=0.20-$^1$H-NMR (300 MHz, $D_2O$): d=1.5 (d, 3H, $J_{6,5}$=6.9 Hz, 6-$H^{Fuc}$), 1.80–2.05 (m, 4H), 3.60–4.50 (m, 16H).

Example 3

Procedure for Preparing the Amines 13a,b

The amine (1 equivalent), triethylamine (2 equivalents) and a catalytic amount of DMAP are added to a solution of the bromine 11 in dichloromethane (3 ml/mmol). The mixture is stirred at room temperature until the reaction is complete, then taken up in dichloromethane and washed with water. After removal of the solvent on a rotary evaporator the residue is purified by flash chromatography (silica gel, isohexane/ethyl acetate 4/1–1/1). The residue is dissolved in MeOH/dioxane/AcoH (5/1/1) and hydrogenated using Pd/C (10%) as catalyst (10 hours). After removal of the catalyst by filtration and removal of the solvent, the oily residue is taken up in 1M sodium hydroxide solution (3–5 ml) and stirred until hydrolysis is complete. The mixture is purified by chromatography (Bakerbond, silica gel RP 18, 40 mm, methanol/water 10/90–90/10).

13a TLC [ethyl acetate/methanol/formic acid/water 5/3/0.5/1]: $R_f$=0.25-$^1$H-NMR (300 MHz, $D_2O$): d=

13b TLC [ethyl acetate/methanol/formic acid/water 5/3/0.5/1]: $R_f$=0.20-$^1$H-NMR (300 MHz, $D_2O$): d=

Example 4

Mannose Derivatives

In a manner similar to that for compound 8, the mannose derivative 14 is prepared as an a/β mixture over 3 stages in 62% yield.

TLC [dichloromethane/methanol:10/1]: $R_f$=0.30-$^1$H-NMR (300 MHz, $D_2O$): d=2.19–2.43 (m, 2H), 3.60–4.00 (m, 7H), 5.05 (m, 2H), 5.62–5.80 (m, 1H).

By benzylation of 14 analogously to compound 9, the allyl compound 15 is prepared. Compound 15 can also be prepared directly by allylating the corresponding benzyl precursor.

TLC [toluene/ethyl acetate:5/1]: $R_f$=0.45-$^1$H-NMR (300 MHz, $CDCl_3$): d=2.35 m, 2 H), 3.60–4.20 (m, 6H), 4.50–4.60 (m, 8H), 4.72 (m, 1H), 5.00 (m, 2H), 5.78 (m, 1H), 7.20–7.40 (m, 20H).

Hydroboration of 15 gives 16.

TLC [toluene/ethyl acetate:1/1]: $R_f$=0.25-$^1$H-NMR (300 MHz, $CDCl_3$): d=1.60 (m, 4H), 3.58–4.05 (m, 9H), 3.50–4.05 (m, 8H).

In a manner similar to that for the fucose derivative 10 the derivatives 17a–c and 18a,b are synthesized from 16.

17a TLC [ethyl acetate/methanol/formic acid/water 5/3/0.5/1]: $R_f$=0.25-$^1$H-NMR (300 MHz, $D_2O$): d=1.40–1.93 (m, 9H), 2.5 (m, 1H), 2.80–3.00 (m, 2H), 3.40–4.12 (m, 10H).

Asparagine Derivative

17b TLC [ethyl acetate/methanol/formic acid/water 5/3/0.5/1]: $R_f$=0.30-$^1$H-NMR (300 MHz, $D_2O$): d=1.40–1.75 (m, 4H), 3.20 (m, 1H), 3.40–3.82 (m, 10H).

Lysine Derivative

17c TLC [ethyl acetate/methanol/formic acid/water 5/3/0.5/1]: $R_f$=0.30-$^1$H-NMR (300 MHz, $D_2O$): d=1.30–1.78 (m, 7H), 3.35–3.80 (m, 15H).

Piperidine Derivative

18 TLC [ethyl acetate/methanol/formic acid/water 5/3/0.5/1]: $R_f$=0.30-$^1$H-NMR (300 MHz, $D_2O$): d=1.38–1.50 (m,1H), 1.60–1.85 (m, 5H), 1.92–2.04 (m, 2H), 230–240 (m, 1H), 2.80–3.15 (m, 4H), 3.22–3.88 (m, 9H).

Example 5

Ribose Derivatives

1-O-Acetyl-2,3,5-tri-O-benzoyl-β-D-ribofuranose (1.0 g, 2.0 mmol) is dissolved in acetonitrile (10 ml) under argon and cooled to −10° C. Following the addition of allylsilane (0.48 ml, 3.0 mmol) and boron trifluoride-diethyl ether complex (0.25 ml, 0.2 mmol) the mixture is stirred at −10° C. for 1 hour. After heating to room temperature, stirring is continued for 2 hours. The solution is poured into saturated sodium hydrogen carbonate solution and subjected to extraction with ethyl acetate. The solvent is removed on a rotary evaporator. The residue which remains is taken up in dichloromethane and filtered through a short silica gel column. Removal of the solvent gives the allyl compound (a/B 4/1) as a yellow oil (0.798 g, 76%).

TLC [hexane/ethyl acetate:1/11: $R_f$=0.60-$^1$H-NMR (300 MHz, $CDCl_3$): d=2.51 (m, 2H), 4.20–6.05 (m, 8H), 7.10–8.35 (m, 15H).

What is claimed is:

1. A compound and its physiologically-compatible salts of the formula I:

wherein:
$R^1$ is —H, $CH_3$ or $CH_2OH$,
$R^2$ is —H or —OH,
$R^3$, $R^4$, and $R^5$ independently of one another are —H, $C_1$-$C_4$-alkyl or —OH,
D is —O—C(O)—, —C(O)— or $NR^6$—C(O)—,
E is —$CR^7R^8$—, —$NR^7$—, or a nitrogen heterocycle of the formula:

n is 1 or 2, m is 0 or 1, p is an integer from 0 to 10, q is 1 or 2, $X^1$ and $X^2$ independently of one another are —H, —COOR$^9$, —NR$^9$R$^{10}$, —OH, OSO$_3$H, —CH$_2$COOR$^9$ or CH$_2$OSO$_3$H or together are =O, and

$R^6$, $R^7$, $R^8$, $R^9$, and $R^{10}$ independently of one another are —H or C$_1$-C$_4$-alkyl, provided that when E is —CR$^7$R$^8$— and each of $R^1$, $R^3$, $R^4$, $R^5$, $R^7$, $R^8$, $X^1$ and $X^2$ is —H, then m is 1.

2. The compound of claim 1 wherein m is 1 and D is —O—C(O)—.

3. The compound of claim 1 wherein m is 0.

4. The compound of claim 1 and its physiologically compatible salts, wherein $R^2$ is —OH and n is 2.

5. The compound of claim 1 and its physiologically compatible salts of the formula:

wherein

A is a sugar radical selected from the group consisting of:

and

6. The compound of claim 1 wherein E is —NR$^7$—, $R^7$ is —H, p is 0, $R^5$ is —H, $X^1$ is —COOR$^9$, $X^2$ is —CH$_2$COOR$^9$ and $R^9$ is —H.

7. The compound according to claim 6 of the formula:

12a

8. The compound according to claim 6 of the formula:

21a

9. The compound according to claim 6 of the formula:

17a

10. The compound according to claim 1 wherein E is —NR$^7$, is —H, p is 4, $R^3$ and $R^4$ are —H, $R^5$ is —H, $X^1$ is —COOR$^9$, $X^2$ is —NR$^9$R$^{10}$ and $R^9$ and $R^{10}$ are —H.

11. The compound according to claim 10 of the formula:

12b

12. The compound according to claim 10 of the formula:

13. The compound according to claim 10 of the formula:

21b

14. The compound according to claim 1 of the formula:

q is 2, p is 0, $R^5$ is —OH and $X^1$ and $X^2$ together are =O.

15. The compound according to claim 14 of the formula:

13a

16. The compound according to claim 14 of the formula:

12c

17. The compound according to claim 14 of the formula:

21c

18. The compound according to claim 14 of the formula:

22a

19. The compound according to claim 14 of the formula:

18a

20. The compound of claim 1 wherein E is a heterocycle of the formula:

q is 2, p is 0, $R^5$ and $R^9$ are —H and $X^1$ and $X^2$ are —COOR$^9$.

21. The compound according to claim 20 of the formula:

12d

22. The compound according to claim 20 of the formula:

23. The compound according to claim 20 of the formula:

21d

24. The compound according to claim 20 of the formula:

22b

25. The compound according to claim 20 of the formula:

13b

26. The compound according to claim 20 of the formula:

27. A process for preparing a compound of formula I according to claim 1, which comprises a) reacting a compound of formula III:

III wherein:

$R^1$ and $R^2$ optionally possess protecting groups, and R is an acetyl group with an allylsilane in the presence of a Lewis acid catalyst to form a compound of formula IV:

IV b) converting the R acetyl group to a benzyl group, followed by;

c) functionalizing the allylic double bond of the compound of formula IV to prepare a compound of formula V:

V wherein $R^1$ and $R^2$ optionally possess protecting groups, R is a benzyl group and Y is halogen or an OH group;

d) reacting the compound of formula V with a compound of the formula:

$$X-E-(CR^3R^4)_p-CR^5X^1X^2$$

wherein

X is —H or —COOH; and e) removing any protecting groups that may be present.

28. A composition comprising a pharmaceutically-acceptable excipient and a physiologically-compatible salt of the formula I:

I wherein:

$R^1$ is —H, $CH_3$ or $CH_2OH$, $R^2$ is —H or —OH, $R^3$, $R^4$, and $R^5$ independently of one another are —H, $C_1$-$C_4$-alkyl or —OH, D is —O—C(O)—, —C(O)— or $NR^6$—C(O)—, E is —$CR^7R^8$—, —$NR^7$—, or a nitrogen heterocycle of the formula:

n is 1 or 2,
m is 0 or 1,
p is an integer from 0 to 10, q is 1 or 2, $X^1$ and $X^2$ independently of one another are —H, —COOR$^9$, —NR$^9$R$^{10}$, —OH, OSO$_3$H, —CH$_2$COOR$^9$ or CH$_2$OSO$_3$H or together are =O, and

R$^6$, R$^7$, R$^8$, R$^9$, and R$^{10}$ independently of one another are —H or C$_1$-C$_4$-alkyl, provided that when E is —CR$^7$R$_8$— and each of R$^1$, R$^3$, R$^4$, R$^5$, R$^7$, R$^8$, X$^1$ and X$^2$ is —H, then m is 1.

29. The composition of claim 28 wherein m is 1 and D is —O—C(O)—.

30. The composition of claim 28 wherein m is 0.

31. The composition of claim 28 comprising a pharmaceutically-acceptable excipient and a physiologically compatible salt
wherein
R$^2$ is —OH and n is 2.

32. The composition of claim 28 comprising a pharmaceutically-acceptable excipient and a physiologically compatible salt of a compound of the formula:

wherein
A is a, sugar radical selected from the group consisting of:

L-fucosyl        D-mannosyl        and ribosyl

33. The composition of claim 28 wherein E is —NR$^7$—, R$^7$ is —H, p is 0, R$^5$ is —H, X$^1$ is —COOR$^9$, X$^2$ is —CH$_2$COOR$^9$ and R$^9$ is —H.

34. The composition according to claim 33 wherein the compound is of the formula:

12a

35. The composition according to claim 28 wherein E is —NR$^7$—, R$^7$ is —H, p is 4, R$^3$ and R$^4$ are —H R$^5$ is —H, X$^1$ is —COOR$^9$, X$^2$ is —NR$^9$R$^{10}$ and R$^9$ and R$^{10}$ are —H.

36. The composition according to claim 35 wherein the compound is of the formula:

12b

37. The composition according to claim 28 wherein E is a heterocycle of the formula:

q is 2, p is 0, R$^5$ is —OH and X$^1$ and X$^2$ together are =O.

38. The composition according to claim 37 wherein the compound is of the formula:

13a

39. The composition according to claim 37 wherein the compound is of the formula:

12c

40. The composition of claim 28 wherein E is a heterocycle of the formula:

q is 2, p I s 0, R$^5$ and R$^9$ are —H and X$^1$ and X$^2$ are —COOR$^9$.

41. The composition according to claim 40 wherein the compound is of the formula:

12d

42. A method of inhibiting selectin-mediated cell adhesion comprising administering to a patient in need thereof an effective amount of a composition which comprises a pharmaceutically-acceptable excipient and a physiologically-compatible salt of a compound of formula I:

I wherein:

$R^1$ is —H, $CH_3$ or $CH_2OH$, $R^2$ is —H or —OH, $R^3$, $R^4$, and $R^5$ independently of one another are —H, $C_1$–$C_4$-alkyl or —OH, D is —O—C(O)—, —C(O)— or $NR^6$—C(O)—, E is —$CR^7R^8$—, —$NR^7$—, or a nitrogen heterocycle of the formula:

n is 1 or 2, m is 0 or 1, p is an integer from 0 to 10, q is 1 or 2, $X^1$ and $X^2$ independently of one another are —H, —$COOR^9$, —$NR^9R^{10}$, —OH, $OSO_3H$, —$CH_2COOR^9$ or $CH_2OSO_3H$ or together are =O, and $R^6$, $R^7$, $R^8$, $R^9$, and $R^{10}$ independently of one another are —H or $C_1$–$C_4$-alkyl, provided that when E is —$CR^7R^8$— and each of $R^1$, $R^3$, $R^4$, $R^5$, $R^7$, $R^8$, $X^1$ and $X^2$ is —H, then m is 1.

43. A method of treating a selectin-mediated disease comprising administering to a patient in need thereof an effective amount of a composition which comprises a pharmaceutically-acceptable excipient and a physiologically-compatible salt of a compound of the formula I:

I wherein:

$R^1$ is —H, $CH_3$ or $CH_2OH$, $R^2$ is —H or —OH, $R^3$, $R^4$, and $R^5$ independently of one another are —H, $C_1$–$C_4$-alkyl or —OH, D is —O—C(O)—, —C(O)— or $NR^6$—C(O)—, E is —$CR^7R^8$—, —$NR^7$—, or a nitrogen heterocycle of the formula:

n is 1 or 2, m is 0 or 1, p is an integer from 0 to 10, q is 1 or 2,

$X^1$ and $X^2$ independently of one another are —H, —$COOR^9$, —$NR^9R^{10}$, —OH, $OSO_3H$, —$CH_2COOR^9$ or $CH_2OSO_3H$ or together are =O, and $R^6$, $R^7$, $R^8$, $R^9$, and $R^{10}$ independently of one another are —H or $C_1$–C4-alkyl, provided that when E is —$CR^7R^8$—and each of $R^1$, $R_3$, $R^4$, $R^5$, $R^7$, $R^8$, $X^1$ and $X^2$ is —H, then m is 1.

44. The method of claim 43 wherein

$R^2$ is —OH and n is 2.

45. The method of claim 43 wherein said compound is of the formula:

wherein

A is a sugar radical selected from the group consisting of:

46. The method of claim 43 wherein E is —$NR^7$, $R^7$ is —H, p is 0, $R^5$ is —H, $X^1$ is —$COOR^9$, $X^2$ is —$CH^2COOR^9$ and $R^9$ is —H.

47. The method of claim 46 wherein the composition administered comprises a physiologically-compatible salt of a compound of the formula:

12a

48. The method according to claim 43 wherein E is —$NR^7$, $R^7$ is —H, p is 4, $R^3$ and $R^4$ are —H, $R^5$ is —H, $X^1$ is —$COOR^9$, $X^2$ is —$NR^9R^{10}$ and $R^9$ and $R^{10}$ are —H.

49. The method according to claim 48 wherein the composition administered comprises physiologically-compatible salt of a compound of the formula:

12b

50. The method according to claim 43 wherein the E is a heterocycle of the formula:

q is 2, p is 0, $R^5$ is —OH and $X^1$ and $X^2$ together are =O.

51. The method according to claim 50 wherein the composition adiminsterd comprises a physiologic-compatible salt of a compound of the formula:

13a

52. The method according to claim 50 wherein the composition adiminsterd comprises a physiologic-compatible salt of a compound physiologically-compatible salt of a of the formula:

12c

53. The method according to claim 43 wherein E is a heterocycle of the formula:

q is 2, p I s 0, $R^5$ and $R^9$ are —H and $X^1$ and $X^2$ are —$COOR^9$.

54. The method according to claim 53 wherein the composition administered comprises a physiologically-compatible salt of a compound of the formula:

12d

55. The method according to any one of claims 43–54 wherein the disease treated is an autoimmune disease.

56. The method of claim 55 wherein the disease treated is selected from the group consisting of acute polyarthritis, rheumatoid arthritis, insulin-dependent diabetes mellitus, acute and chronic transplant rejections and adult respiratory distress syndrome (ARDS).

57. The method according to any one of claims 43–54 wherein the disease treated is an inflammatory and allergic skin disease.

58. The method according to claim 57 wherein the disease treated is selected from the group consisting of psoriasis and contact eczema.

59. The method according to any one of claims 43–54 wherein the disease treated is a cardiovascular disease.

60. The method according to claim 59 wherein the disease treated is selected from the group consisting of myocardial infarction, reperfusion injury, septic shock and systemic shock.

* * * * *